United States Patent [19]
Lang

[11] Patent Number: 5,810,883
[45] Date of Patent: Sep. 22, 1998

[54] MEDICAL FORCEPS

[75] Inventor: Dieter Lang, Stockheim, Germany

[73] Assignee: Karl Storz GmbH & Co., Germany

[21] Appl. No.: 812,295

[22] Filed: Mar. 7, 1997

[30] Foreign Application Priority Data

Mar. 7, 1996 [DE] Germany .................. 196 08 768.6

[51] Int. Cl.⁶ .................................................. A61B 17/00
[52] U.S. Cl. ..................... 606/207; 606/174; 600/564
[58] Field of Search .................... 606/1, 51, 52, 606/83, 170, 205–210; 128/750–755; 600/562–567

[56] References Cited

U.S. PATENT DOCUMENTS

| | | |
|---|---|---|
| 1,754,806 | 4/1930 | Stevenson . |
| 4,243,047 | 1/1981 | Olsen . |
| 4,522,206 | 6/1985 | Whipple et al. . |
| 4,994,024 | 2/1991 | Falk ........................................... 606/83 |
| 5,395,375 | 3/1995 | Turkel et al. ............................. 606/83 |

FOREIGN PATENT DOCUMENTS 37 36 150 A1  5/1989  Germany .

OTHER PUBLICATIONS

"Karl Storz–Endoskope, endoskopische Chirurgie" [Karl Storz endoscopes, endoscopic surgery], section 5, p. SCT 5/4 A(Frangenheim forceps), 2nd edition, Jan. 1994, of Karl Storz GmbH & Co., Tuttlingen, Germany.

*Primary Examiner*—William Lewis
*Attorney, Agent, or Firm*—St. Onge Steward Johnston & Reens LLC

[57] ABSTRACT

A medical forceps, which is used in particular for detaching bone or cartilage tissue in the frontal sinus, has a handle, a shaft, an immovable jaw part and a movable jaw part both attached to the distal end of the shaft. An articulation element serves for rotatably moving the movable jaw part about the immovable jaw part. Said immovable jaw part is provided with a recess continuing over the entire width of said immovable jaw part. A section of said movable jaw part at which section said actuation element is connected to said immovable jaw part is arranged in said recess allowing said section of said movable jaw part to extend over the entire width of said immovable jaw part.

8 Claims, 5 Drawing Sheets

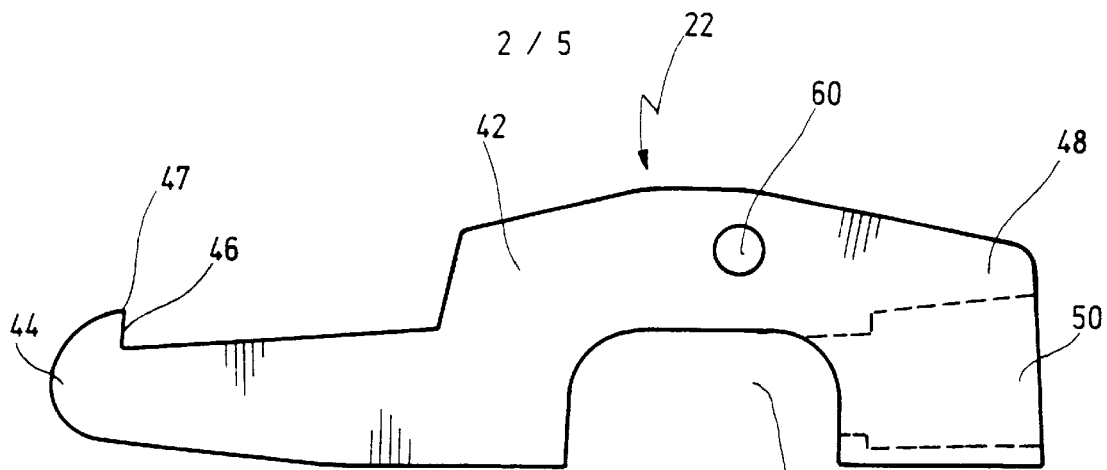
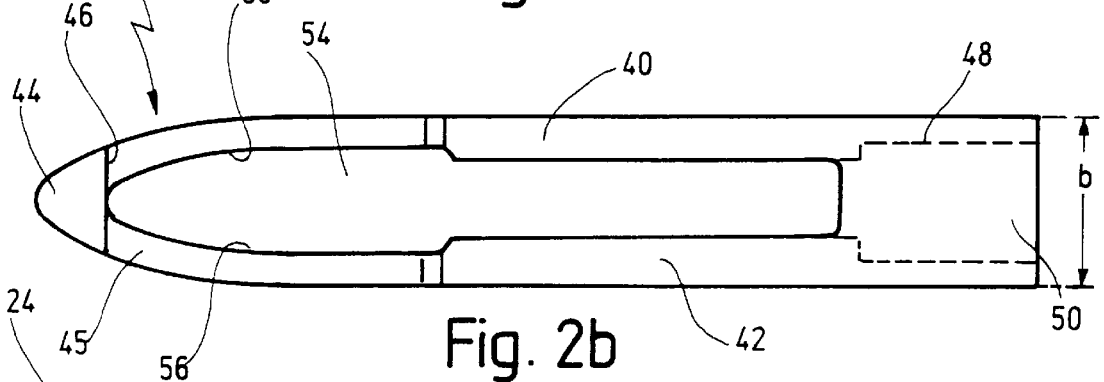
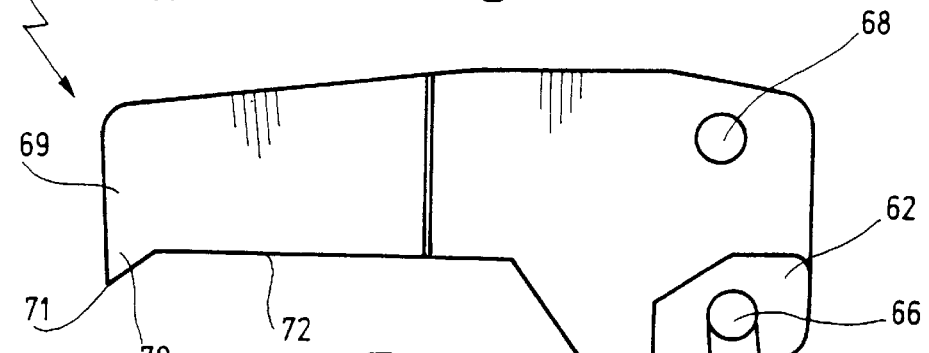
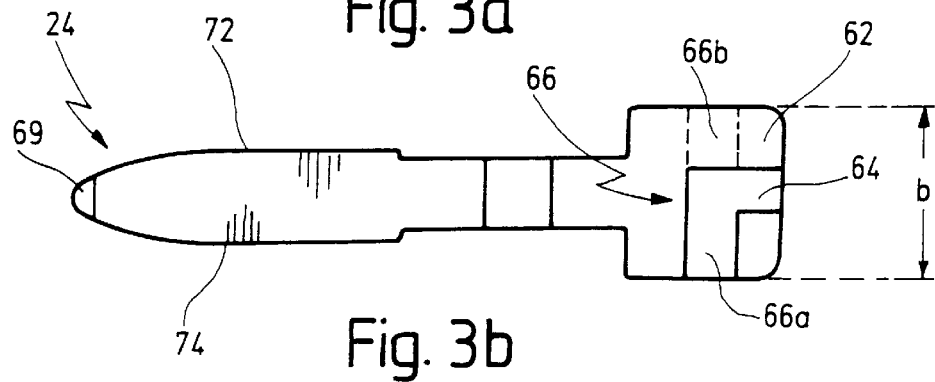

MEDICAL FORCEPS

BACKGROUND OF THE INVENTION

1. Field of the Invention

The present invention relates to a medical forceps, in particular for detaching bone or cartilage tissue in the frontal sinus, having an immovable jaw part and a movable jaw part attached thereon about a rotation axis. A handle has a movable handle element. An actuation element is connected to said movable handle element at one end and is connected at its opposite end to said movable jaw part.

2. Prior Art

A forceps of this kind is known from the German brochure "Karl Storz-Endoskope, endoskopische Chirurgie" [Karl Storz endoscopes, endoscopic surgery], section 5, page SCT 5/4 A (FRANGENHEIM forceps), 2nd edition, January 1994, of Karl Storz GmbH & Co., Tuttlingen, Germany.

In endoscopic surgery, a forceps of this kind is used to remove pathological excess bone tissue. A further application which often occurs is removal of excess bone tissue in the frontal sinus. In the surgical operation, the forceps is introduced with its jaw parts into the relevant operative area through the nasal opening and an artificially created opening (called a "window") in the nasal septum. However, not only the window but also the operative area in the frontal sinus are very confined, so that the forceps must have extremely small forceps jaw parts which not only must fit in the confined operative area, but also must be opened prior to cutting in order to detach the bone tissue.

The known forceps has a long shaft at whose distal end, i.e. the end nearest the patient, the jaw parts are arranged, and at whose end remote from the patient two handle elements are arranged. Of the two jaw parts, one is joined immovably to the shaft, while the other jaw part is movable relative to the immovable jaw part in order to open and close the forceps. For that purpose, the movable jaw part is joined via an actuation element to a movable handle element at the end remote from the patient. The jaw parts are opened by pressing the handle elements apart, and closed in order to detach tissue by pressing them together.

The immovable jaw part has two limbs between which the immovable jaw part is pivotably arranged. The limbs extend parallel to one another as far as the end nearest the patient, and at that end are joined together by a strut extending transverse to the limbs. In the known forceps, the movable jaw part, at its end remote from the patient at which the actuation element is attached to the movable jaw part, is completely enclosed by the limbs of the immovable jaw part in the manner of a housing.

While the immovable jaw part determines the outside dimensions of the forceps in the region of the jaw parts when the jaw parts are closed, the movable jaw part is configured correspondingly more narrowly, since the latter, being received between the limbs, is only as wide as the gap between the limbs of the immovable jaw part.

Since, as already mentioned, during a surgical operation the forceps is inserted with the jaw parts through a window into the confined operative area of the frontal sinus, it is necessary to maintain a minimum physical size for the forceps, in particular in the region of the forceps jaw parts, in order to achieve better handling of the forceps in the operative area. In the case of the known forceps, however, miniaturization of the forceps in the region of the jaw parts would mean that the movable jaw part would need to be made narrower to the same degree. Since the actuation element is also articulated on the movable jaw part, limits are placed on the desire for increasingly small dimensions of the jaw parts by the fact that the cross section of the movable jaw part, on which the actuation element is articulated and on which the entire manual force exerted by the operator on the handle elements therefore acts, must reliably withstand these high loads. A considerable transfer of force to the forceps jaw parts is required specifically to detach bone tissue, so that the movable jaw part must be highly stable particularly in the articulation region of the actuation element, to prevent the actuation element from being torn out of the movable jaw part during the operation.

In the case of the known forceps, the overall width in the region of the jaw parts is between 3.5 and 5 mm. For surgical operations in children, forceps with even less overall width are required; specifically, the overall width and overall height of such forceps should be approximately 1.5 to 2.5 mm. With the known design for such medical forceps, however, there exists the disadvantage that such small overall size leads to a considerable weakening of the region surrounded in the manner of a housing on which the actuation element is articulated, so that the stability of the forceps in this region of the jaw parts is reduced to less than the required magnitude.

U.S. Pat. No. 4,522,206 discloses a surgical instrument for detachment of pieces of tissue whose immovable jaw part is joined integrally to the shaft, while the movable jaw part is attached pivotably about an articulation axis on the immovable jaw part. The shaft terminates at its end nearest the patient, on the side opposite the immovable jaw part, at an edge. A longitudinally extending slot, in which the region of the movable jaw part at which the actuation element is articulated on the latter is arranged, extends in the shaft from the edge to the end nearest the patient. The slot is narrower than the diameter of the tubular shaft. With this known forceps, the articulation region of the movable jaw part is once again laterally enclosed by the shaft in the region of the slot.

DE 37 36 150 A1 also describes a forceps that has a movable jaw part attached pivotably on an immovable jaw part. The immovable jaw part is joined integrally to the shaft and is constituted by two limbs joined at the end nearest the patient. This configuration of the jaw parts therefore results in a through-cutting forceps. The movable jaw part, which is joined to the movable handle element via a push/pull rod, is arranged between the limbs of the immovable jaw part. The region of the movable jaw part to which the push/pull rod is attached is arranged between the limbs of the immovable jaw part and surrounded by the limbs in the manner of a housing.

A further forceps of this kind has been disclosed by U.S. Pat. No. 4,243,047, in which the movable jaw part, as in the forceps mentioned earlier, is arranged between two limbs of the immovable jaw part, the region of the movable jaw part on which the actuation element is articulated being once again enclosed in the manner of a housing by the limbs of the immovable jaw part.

Also known from U.S. Pat. No. 1,754,806 is a surgical forceps, in particular for the removal of bone tissue from the frontal sinus, in which the movable jaw part is arranged between two limbs of the immovable jaw part, and in which the actuation element can be attached to a section of the movable jaw part that is arranged completely between the limbs of the immovable jaw part.

In all of the forceps mentioned above, there still exists the problem that the region of the movable jaw part on which the actuation element is articulated is reduced in strength, which when such forceps are miniaturized leads to a loss in stability of this region that is surrounded in the manner of a housing.

SUMMARY OF THE INVENTION

It is therefore the object of the present invention to develop a medical forceps of the kind cited initially in such a way that the narrowest possible physical embodiment of the forceps in the region of the jaw parts, but nevertheless high stability of the forceps, is achieved, so that the large forces necessary to detach bone or cartilage tissues can be transferred to the jaw parts even with such narrow forceps.

According to the invention the object is achieved, with regard to the medical forceps cited initially, by the fact that a recess continuing over the entire width of the immovable jaw part is configured in the immovable jaw part; and said section of the movable jaw part at which the actuation element is articulated on the movable jaw part is arranged in the recess. Therefore said section can be extended in the region of the recess over the entire width of the immovable jaw part.

Because of the recess in the immovable jaw part which extends over the entire width of the immovable jaw part, and because the section of the movable jaw part at which the actuation element is articulated on the movable jaw part is arranged specifically in said recess, and said section extends over the entire width of the immovable jaw part, the entire available width of the immovable jaw part is advantageously utilized in order to configure the part of the movable jaw part that is critical for force transfer, namely the articulation region for the actuation element, in as broad and solid a fashion as possible. While the recess in the immovable jaw part does not cause any loss in stability of the immovable jaw part, on the other hand the reinforcement of the section of the movable jaw part on which the actuation element is articulated, said reinforcement extending over the entire available width of the movable jaw part, leads to a considerable increase in the stability of the movable jaw part. The configuration of the jaw parts according to the invention makes it possible to reduce the overall size of the jaw parts without decreasing the stability thereof, as is the case with the forceps that are known in the art.

In a preferred embodiment, the section of the movable jaw part has a T-shaped cutout in which a pin of the actuation element is held in lossproof fashion, the transverse region of the T-shaped cutout extending over the entire width of the section.

It is a first advantage of this feature that a connection is created between the actuation element and the movable jaw part in which additional parts such as pegs or studs, which usually prove to be defined breaking points, are omitted. Because the transverse region of the T-shaped cutout extends over the entire width of the section of the movable jaw part, the further advantage is achieved that the pin of the actuation element can also be configured so that it extends over the entire available overall width. Thus the actuation element also meets the stringent stability requirements, so that as a whole, a forceps suitable for the application of large forces is created. Particularly high stability of the actuation element results if the actuation element with its pin is worked out of a solid material.

In a further preferred embodiment, the rotation axis and the connection point between the movable jaw part and the actuation element are arranged with respect to one another in such a way that an angle in the range of approximately 80 to 100 degrees is present between a longitudinal axis of the actuation element and a connecting line between the rotation axis and the connection point when the jaw parts are opened and closed.

Since the connection point represents the point at which the force transferred via the actuation element and causing pivoting of the movable jaw part about the rotation axis acts on the movable jaw part, the result of this arrangement of rotation axis and force action point with respect to the pulling direction of the actuation element is a particularly advantageous transfer of force to the jaw parts. Since the forceps according to the invention is used in particular to detach bone tissue, which requires considerable force, the arrangement according to the invention of the rotation axis and the pivot point of the actuation element amplifies the manual force of the operator in lever fashion.

In a further preferred embodiment, the movable jaw part and the immovable jaw part each have a sharp claw at their ends nearest the patient, such that with the jaw parts in a position in which the tips of the claws just touch, the angle is approximately 90 degrees.

The advantage of this feature is that with the jaw parts in the position in which the two claws are coacting in order to pick off a bone fragment, the tensile force is acting at a right angle on the lever constituted between the rotation point and the transverse region of the T-shaped cutout of the movable jaw part, thus maximizing the torque and thus the lever effect. The sharp claws moreover have the advantage that the force at the tips acts in almost point fashion on the bone tissue, thus picking off the bone fragment with high pressure.

In a further preferred embodiment, the movable jaw part and the immovable jaw part are each worked out of a solid material.

The advantage of this feature is that the two jaw parts inherently have very high stability because connecting weld beads or spots, which usually represent defined breaking points, are avoided.

In a preferred embodiment of the invention, the immovable jaw part has, at least in the region of the rotation axis, two limbs between which the movable jaw part is arranged.

The advantage of this feature is that the movable jaw part experiences stable lateral guidance between the limbs, thus preventing the movable jaw part from deviating laterally when cutting hard tissues such as bone. Another advantage achieved is that the rotation axis which represents the connection between the movable and immovable jaw parts is mounted in secure and stable fashion in the limbs.

In a preferred embodiment, the limbs converge to a tip toward the end nearest the patient.

This feature is particularly advantageous in the case of a surgical operation in the frontal sinus. Since the entry opening into the frontal sinus is very narrow, the tip can be used to probe the entry opening gently, while with the region of the jaw parts remote from the patient, which spreads out slightly, said opening is correspondingly widened so that the forceps can then easily be introduced into the frontal sinus. The forceps according to the invention is thus further improved in terms of handling in the operative area.

In a further preferred embodiment, the forceps has a tubular shaft that has a curved region at the end nearest the patient, the immovable jaw part being joined to the shaft directly in the curved region.

It has been found that handling of the forceps in the case of an endoscopic surgical operation in the frontal sinus is improved if the shaft is curved at the end nearest the patient.

According to the invention, the immovable jaw part is joined to the shaft directly in the curved region, thus resulting in the advantage that the jaw parts directly continue the curved region without losing the advantages of the curvature due to a long, straight attachment extension provided on the shaft or on the immovable jaw part.

Further advantages are evident from the description below and the appended drawings.

It is understood that the features mentioned above and those yet to be explained below can be used not only in the respective combinations indicated, but also in other combinations or in isolation, without leaving the context of the present invention.

An exemplified embodiment of the invention is depicted in the appended drawings and will be explained in more detail in the description below.

BRIEF DESCRIPTION OF THE DRAWINGS

In the drawings:

FIGS. 2a–b show a side view and a plan view (2b) of the immovable jaw part of the forceps of FIG. 1, as an individual part;

FIGS. 3a–b show a side view and a view from below (3b) of the movable jaw part of the forceps of FIG. 1, as an individual part;

DESCRIPTION OF PREFERRED EMBODIMENTS

Figure 1:
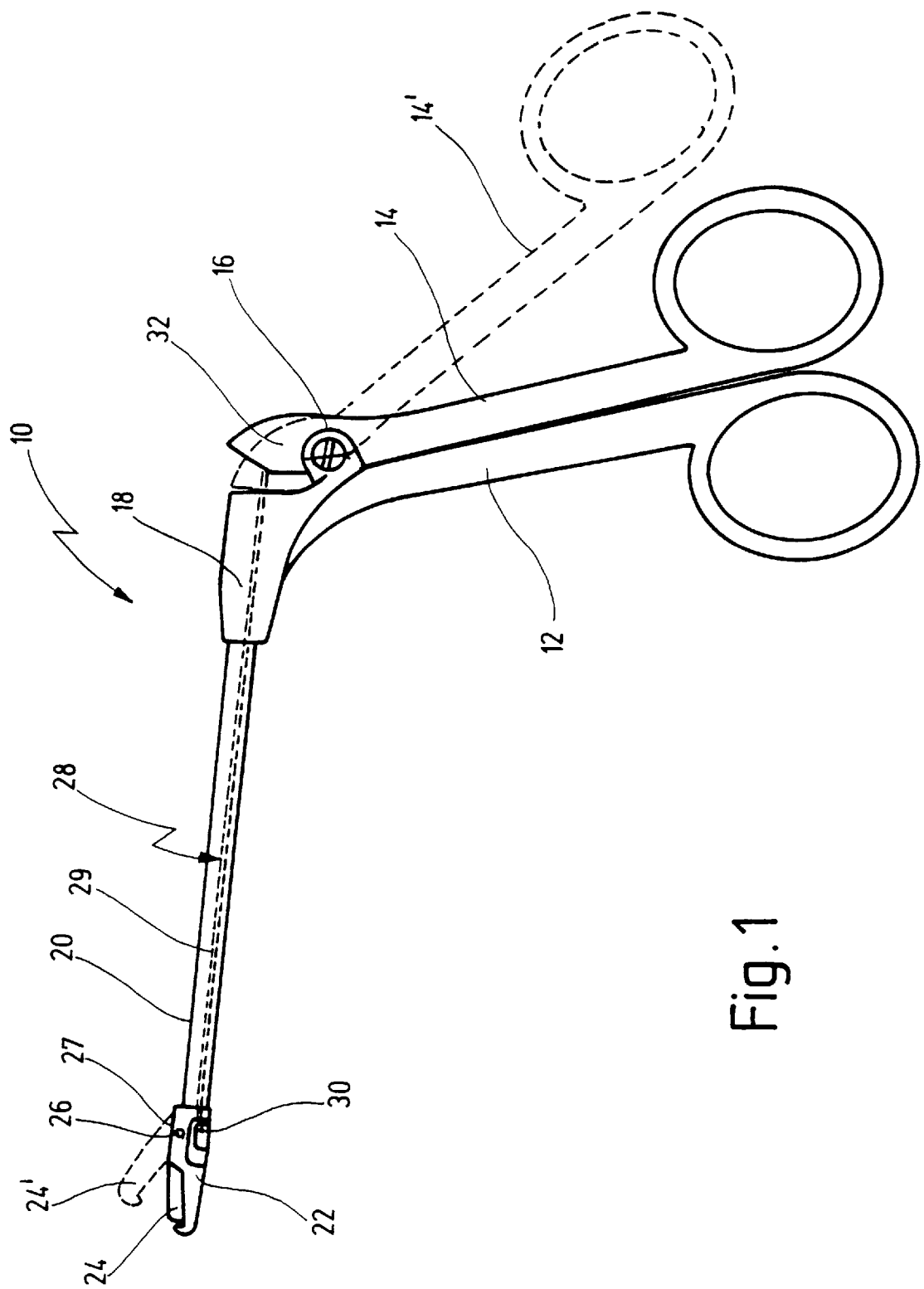
FIG. 1 shows a side view of a medical forceps in two working positions.

FIG. 1 shows a medical forceps designated as a whole with the reference character 10. Forceps 10 is used to remove bone or cartilage tissue in the frontal sinus.

Provided at the end of forceps 10 remote from the patient are an immovable handle element 12 and a movable handle element 14, which are joined together via a hinge joint 16; specifically, movable handle element 14 can be pivoted about hinge joint 16, as the rotation axis, into an open position depicted with dashed lines at 14'. An elongated tubular shaft 20 leads from an end region 18 of immovable handle element 12. Handle elements 12 and 14 and shaft 20 are manufactured from a metal or a plastic with comparable properties.

Arranged at the end of shaft 20 nearest the patient are an immovable jaw part 22 and a movable jaw part 24. Immovable jaw part 22 is permanently joined to shaft 20. Movable jaw part 24 is attached pivotably on immovable jaw part 22 via a pivot pin 26 as rotation axis 27, as will be explained later in further detail.

Movable jaw part 24 is joined nonpositively, via an actuation element 28, to movable handle element 14. Actuation element 28 has a wire sheath 29 which has at its end nearest the patient a pin 30 that extends transverse to wire sheath 29. Pin 30 is worked, together with wire sheath 29, out of a solid material, specifically a hardened steel.

Pin 30 engages into a corresponding opening of movable jaw part 24, as will also be explained later in further detail. Actuation element 28 extends from movable jaw part 24 into shaft 20, through end region 18 of immovable handle element 12, to an end region 32 of movable handle element 14, where it is attached by means of attachment means not depicted here.

FIG. 1 further depicts, at 24', the opened position of movable jaw part 24 that is attained by moving movable handle element 14 into the position designated 14'. Pressing handle elements 12 and 14 together thus causes jaw parts 22 and 24 to close.

FIGS. 2a and 2b, and 3a and 3b, show immovable jaw part 22 and movable jaw part 24 as individual parts at greatly enlarged scale.

Immovable jaw part 22 is, in its entirety, worked integrally out of a solid material.

Immovable jaw part 22 has two laterally arranged limbs 40 and 42 which converge at the end nearest the patient to a tip 44. For this purpose, limbs 40 and 42 are curved toward the longitudinal center axis in a region 45. Tip 44 has a claw 46 which has a cutting edge 47.

At the end remote from the patient, limbs 40 and 42 are joined together by an end section 48 in which an approximately cylindrical bore 50 is provided, the contour of which is indicated with dashed lines in FIGS. 2a and 2b. As is evident from FIGS. 5a to 5c, immovable jaw part 22 is slid, with bore 50, onto the end nearest the patient of shaft 20, and fastened thereto by, for example, soldering.

Limbs 40 and 42 of immovable jaw part 22 furthermore have a recess 52 that is provided in both limb 40 and limb 42. Recess 52 thus extends over the entire width of jaw part 22.

Between limbs 40 and 42, end section 48, and tip 44 with claw 46, immovable jaw part 22 has an opening 54 that continues through from the upper side of jaw part 22 to the lower side.

The inner edges of limbs 40 and 42 of immovable jaw part 22, facing opening 54, are configured as sharp cutting edges 56 and 58, cutting edge 47 of claw 46 projecting upward beyond cutting edges 56 and 58.

Also provided in each of limbs 40 and 42 above recess 52 is a bore 60 into which pivot pin 26 of FIG. 1 can be inserted in order to attach movable jaw part 24 in immovable jaw part 22 pivotably between limbs 40 and 42.

Figure 4A:
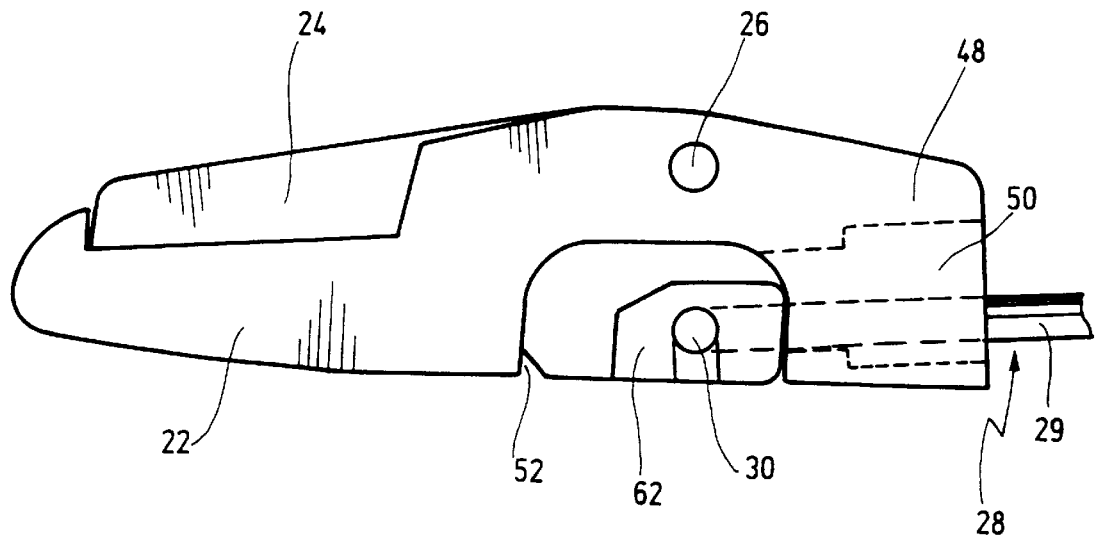
FIGS. 4a–b each show a side view of the assembled jaw parts of FIGS. 2 and 3, in various working positions.
Figure 4B:
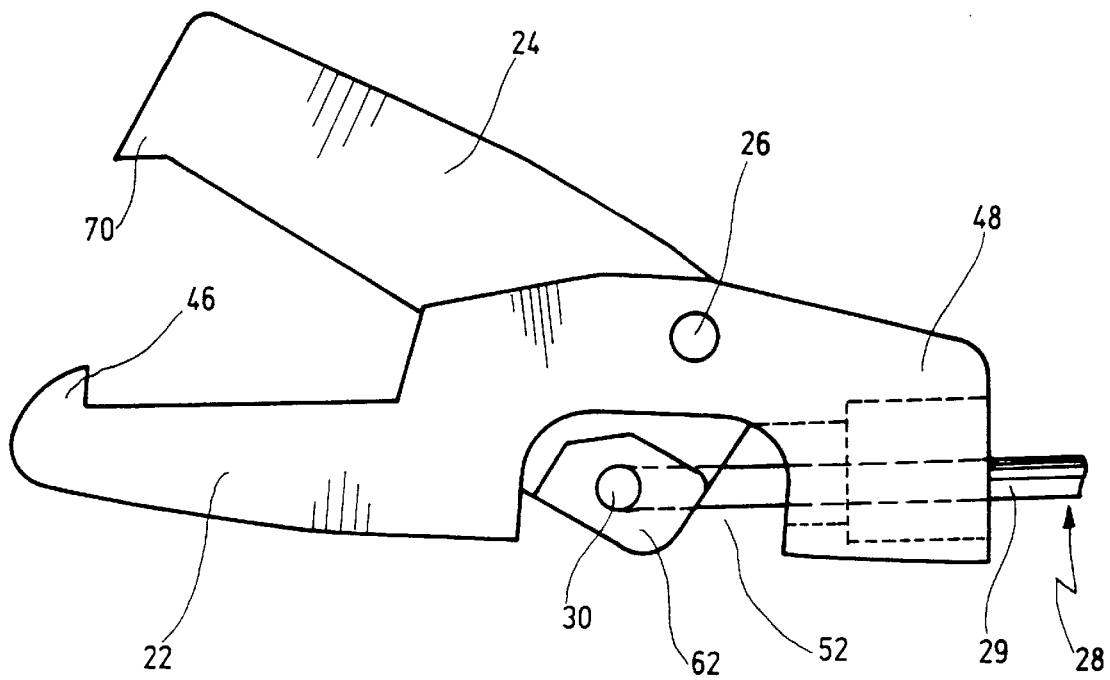

Movable jaw part 24 is depicted in FIGS. 4a and 4b. Movable jaw part 24 is, in its entirety, worked integrally out of a solid material. Movable jaw part 24 has at the end remote from the patient a section 62 on which actuation element 28 is articulated with pin 30 on movable jaw part 24. Section 62 has a width b that is approximately equal to width b of immovable jaw part 22. Width b is approximately 1.5 mm.

A T-shaped cutout that is constituted by a longitudinal section 64 and a transverse region 66 is provided in section 62.

Figure 5A:
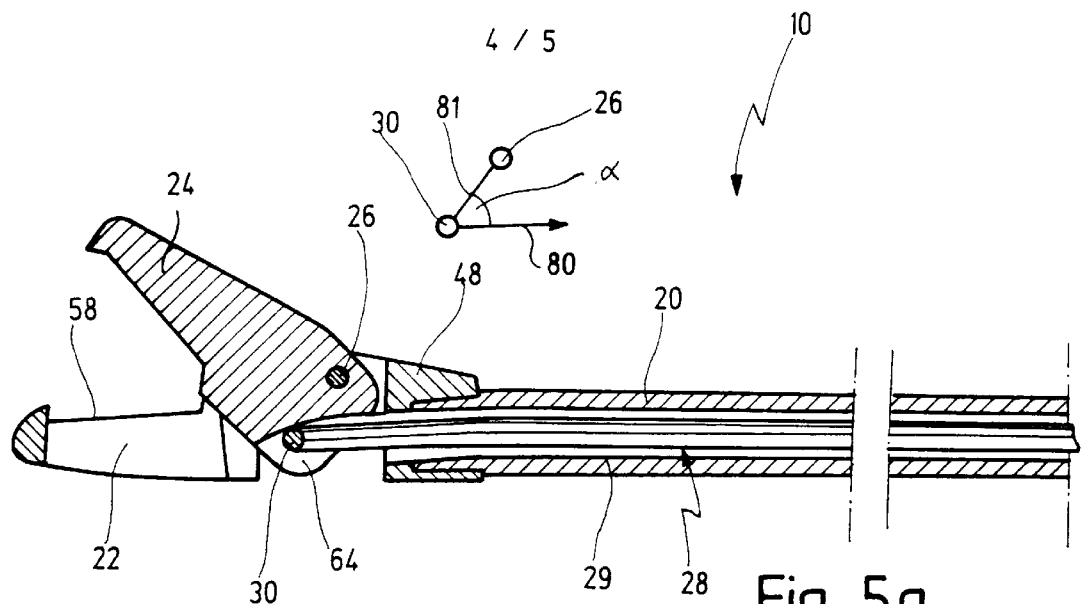
FIGS. 5a–c show a longitudinal section through the end nearest the patient of the forceps of FIG. 1, in three working positions.

Longitudinal section 64, which is better seen in FIG. 5a, is cut deeply into jaw part 24, i.e. it extends from the underside of movable jaw part 24 upward to the back side, remote from the patient, of movable jaw part 24.

Transverse region 66 of the T-shaped cutout extends perpendicular to longitudinal section 64 over the entire width b of movable jaw part 24. While transverse region 66 extends in a section 66a to the underside of movable jaw part 24, transverse region 66 is configured on the side opposite section 66a as a bore 66b that is spaced away from the underside of movable jaw part 24 and therefore is not visible in the depiction of FIG. 3b, but rather is depicted only with dashed lines.

When jaw parts 22 and 24 are in the assembled state, pin 30 of actuation element 28 is held in lossproof fashion in the T-shaped cutout. Pin 30 of actuation element 28 has, in this context, a width which corresponds to width b of immovable jaw part 22.

Provided in movable jaw part 24 above section 62, specifically approximately above transverse region 66 of the T-shaped cutout, and spaced away therefrom, is a bore 68 through which pivot pin 26 of FIG. 1 can be inserted.

Movable jaw part 24 tapers at the end nearest the patient to a tip 69, and has a claw 70 with a cutting edge 71 which coacts with claw 46 of immovable jaw part 22 in order to pick off a bone fragment. The lower outer edges of movable jaw part 24 are configured as cutting edges 72 and 74, which coact with cutting edges 56 and 58 of immovable jaw part 22 in order to cut off the bone fragment that has already been picked loose.

As is evident from FIG. 3b, movable jaw part 24 has, outside section 62, a contour which corresponds to the contour of opening 54 in immovable jaw part 22.

In terms of its vertical extension, as well, movable jaw part 24 is exactly as high as permitted by stability requirements. While having a low overall height that still meets stability requirements, movable jaw part 24 can be opened further in the operative area, thus improving the handling of the forceps.

FIGS. 4a and 4b depict movable jaw part 24 and immovable jaw part 22 in the assembled state. Movable jaw part 24 is arranged between limbs 40 and 42 of immovable jaw part 22, pivot pin 26 being inserted through bores 60 of limbs 40 and 42 and through bore 68 of immovable jaw part 22. Section 62 of immovable jaw part 22 is arranged in recess 52 of movable jaw part 24. Pin 30 of actuation element 28 is suspended in the T-shaped cutout.

FIG. 4a shows jaw parts 22 and 24 in the closed position. Section 62 is thus located at the end remote from the patient of recess 52, and rests with its side remote from the patient against the side remote from the patient of recess 52. It is evident from FIG. 4a that movable jaw part 24 has the same overall height as immovable jaw part 22.

FIG. 4b shows jaw parts 22 and 24 in an open position, in which section 62 of movable jaw part 24 is pivoted toward the end nearest the patient about pivot pin 26. Section 62 of movable jaw part 24 has a height, and extends a distance in the longitudinal direction, which make possible sufficient pivoting of movable jaw part 24 to open jaw parts 22, 24.

Figure 5B:
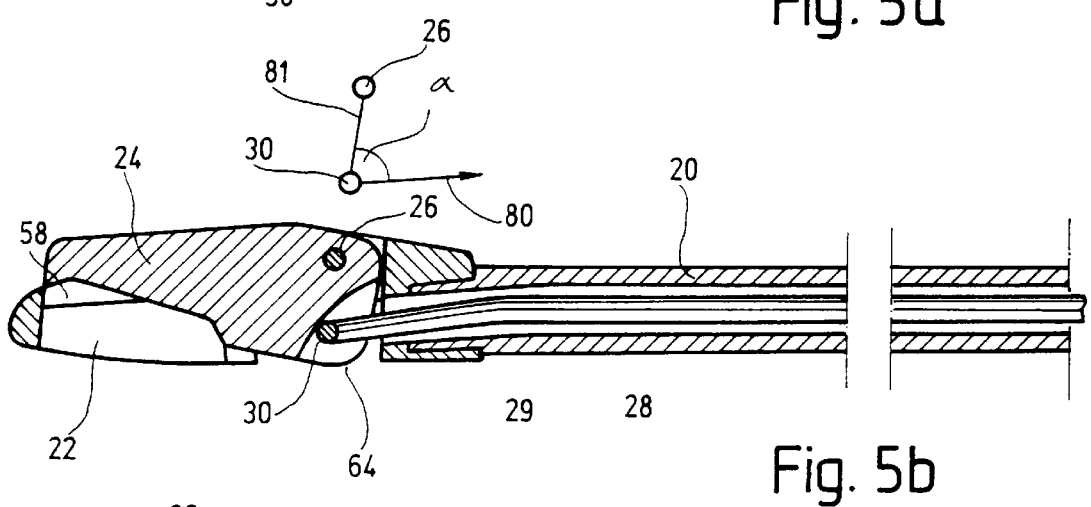
Figure 5C:
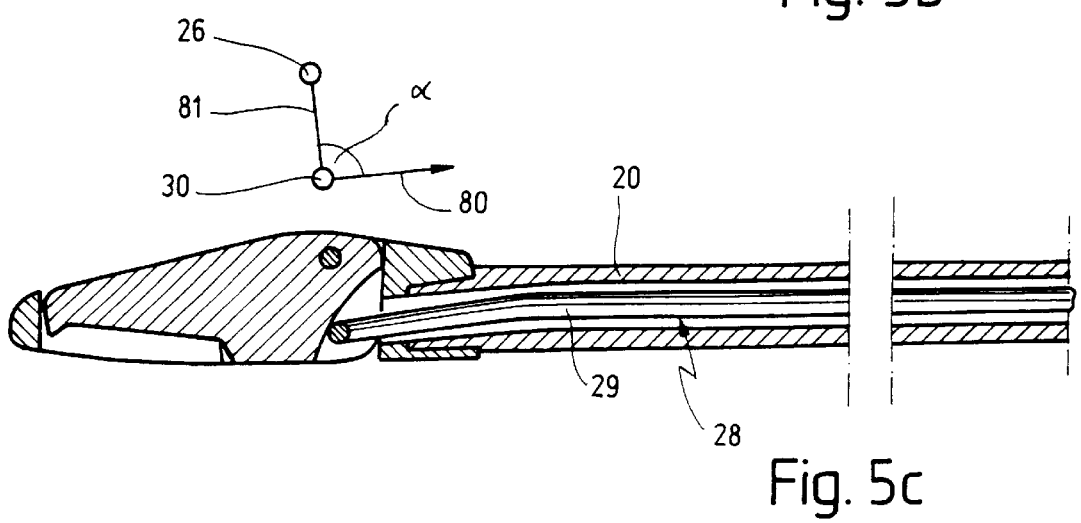

FIGS. 5a to 5c show the end nearest the patient of forceps 10, in a section through the longitudinal center plane of forceps 10.

FIG. 5a shows forceps 10 in an operating state in which jaw parts 22 and 24 are maximally open. In this position, pin 30 of actuation element 28 is displaced toward the end nearest the patient with respect to stationary pivot pin 26. It is clearly evident here that the deeply cut-in longitudinal section 64 in jaw part 24 makes it possible for jaw part 24 to pivot about stationary wire sheath 29 of actuation element 28.

A connecting line 81 between pivot pin 26, which defines the rotation axis for pivoting of movable jaw part 24 with respect to jaw part 22, and pin 30, forms, with a pull direction or longitudinal axis 80 of actuation element 28, an angle α that, with jaw parts 22 and 24 in this position, is approximately 80 degrees. Connecting line 81 constitutes a lever arm on which actuation element 28 engages with pin 30 and pivots the latter about pivot pin 26 acting as rotation axis.

FIG. 5b shows a working position of forceps 10 in which movable jaw part 24 assumes a position in which tip 71 of claw 70 just touches edge 47 of claw 46. In this position of movable jaw part 24, angle α is approximately 90 degrees. In this position, in which the bone fragment to be removed is broken loose using claws 70 and 46, the lever effect is therefore maximal, so that the manual force of the operator is maximally amplified in this position. As handle elements 12 and 14 are pressed further together, the bone fragment broken loose by claws 70 and 46 is then cut through along cutting edges 56 and 58, and 72 and 74, and completely detached.

FIG. 5c depicts the end of the cutting process, in which jaw parts 22 and 24 have assumed their closed position. In this state, pin 30 of actuation element 28 is located behind pivot pin 26, displaced toward the end of forceps 10 remote from the patient. In this closed position, angle α is approximately 95 degrees.

Figure 6:
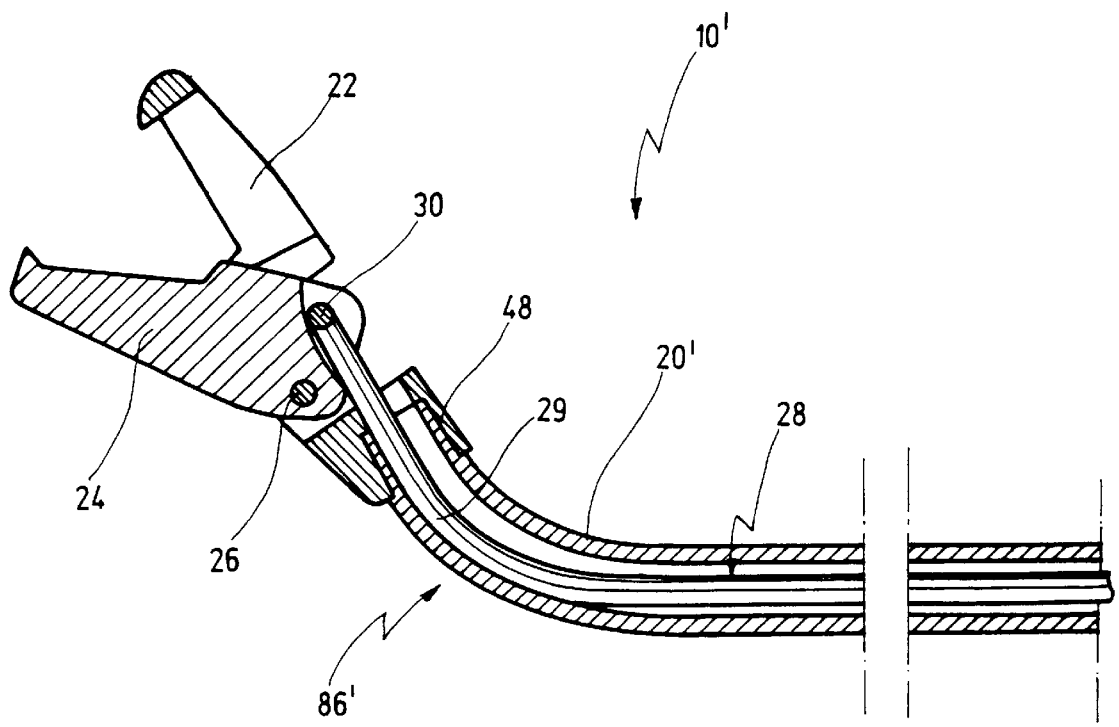
FIG. 6 shows a longitudinal section through the end nearest the patient of an exemplified embodiment altered as compared to the forceps of FIG. 1.
Figure 7:
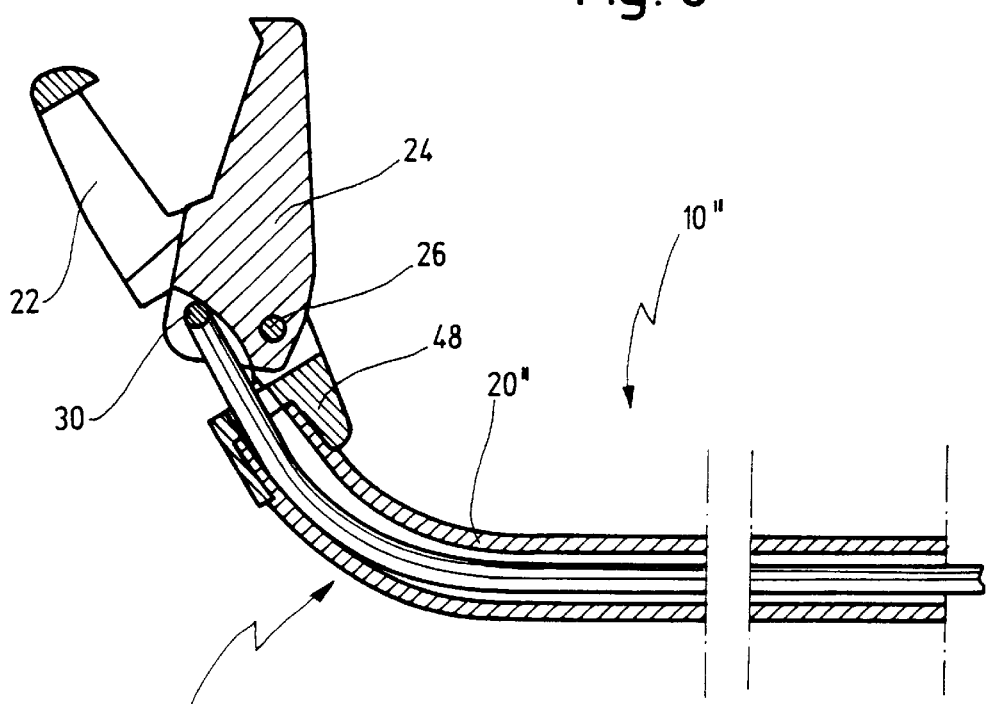
FIG. 7 shows a longitudinal section through the end nearest the patient of a further exemplified embodiment, similar to FIG. 6.

FIGS. 6 and 7 show medical forceps 10' and 10" which, as compared to medical forceps 10, have a shaft 20' and 20". Shafts 20' and 20" have a curved region 86' and 86" at the end nearest the patient. Immovable jaw part 22 is attached, with end section 48, directly to shafts 20' and 20" in curved region 86' and 86", by the fact that end section 48 is slid with its bore 50 onto curved region 86', 86" of shafts 20' and 20" and immobilized by a solder join. Bore 50 extends as deeply as possible into end section 48 so that movable jaw part 24 comes to rest as close as possible to the end of curved region 86', 86" nearest the patient; as a result, as is particularly apparent with the arrangement according to FIG. 7, the open jaw part 24 continues the arc described by curved region 86".

In the case of medical forceps 10' according to FIG. 6, jaw parts 22 and 24 are arranged such that movable jaw part 24 opens toward the outside of curved region 86' of shaft 20'.

In the case of medical forceps 10" according to FIG. 7, the reverse situation is depicted, such that movable jaw part 24 opens toward the inside of curved region 86" of shaft 20".

What is claimed is:

1. A medical forceps, comprising
    a handle having a movable handle element and an immovable handle element,
    a shaft connected to said immovable handle element,
    an immovable jaw part disposed at a distal end of said shaft,
    a movable jaw part, rotatably attached to said immovable jaw part about a rotation axis,
    an actuation element connected to said movable handle element at one end and connected to a section of said movable jaw part at an opposite end thereof via an articulation,
    wherein said immovable jaw part is provided with a recess continuing over an total outer width of said immovable jaw part, and
    wherein said immovable jaw part is provided with a recess continuing over an total outer width of said immovable jaw part, and
    wherein said section of said movable jaw part, at which section said actuation element is connected to said movable jaw part is arranged in said recess, thereby allowing said section of said movable jaw part to extend over the total outer width of said immovable jaw part.

2. The medical forceps of claim 1, wherein said section of said movable jaw part is provided with a T-shaped cutout, in which cutout a pin of said actuation element is held in lossproof fashion, a transverse region of said T-shaped cutout extending over the entire width of said section.

3. The medical forceps of claim 1, wherein said rotation axis and a point at which said movable jaw part is connected to said actuation element are arranged with respect to one another in such a way that an angle α in the range of about 80 to about 100 degrees is present between a longitudinal axis of said actuation element and a connecting line connecting said rotation axis with a point, at which said immovable part is connected to that actuation element, said range of about 80 to 100 degrees is present when said jaw parts are opened and closed.

4. The medical forceps according to claim 3, wherein said movable jaw part and said immovable jaw part each have a claw at their distal ends, and in a closed position of said two jaw parts, at which closed position cutting edges of said claws just touch, said angle α is approximately 90 degrees.

5. The medical forceps of claim 1, wherein both the movable jaw part and the immovable jaw part are worked integrally out of a solid material.

6. The medical forceps of claim 1, wherein said immovable jaw part is provided, at least in the region of the rotation axis, with two limbs, said movable jaw part is arranged between said two limbs.

7. The medical forceps of claim 6, wherein said limbs converge to a tip toward the distal end.

8. The medical forceps of claim 1, wherein said forceps is provided with a tubular shaft having a curved distal end, and the immovable jaw part being joined to said curved tubular shaft immediately to said curved region.

\* \* \* \* \*